US00RE41253E

(19) United States
(12) Reissued Patent
Considine et al.

(10) Patent Number: US RE41,253 E
(45) Date of Reissued Patent: Apr. 20, 2010

(54) ANTINEOPLASTIC COMBINATIONS

(75) Inventors: John Leo Considine, Bridgewater, NJ (US); Sylvain Daigneault, Laval (CA); Warren Chew, Pierrefonds (CA); Silvio Iera, Montreal (CA); Scott Duncan, Madison, WI (US); Jiaxin Ren, Nanuet, NY (US)

(73) Assignee: Wyeth, Madison, NJ (US)

(21) Appl. No.: 11/978,093

(22) Filed: Oct. 26, 2007

Related U.S. Patent Documents

Reissue of:
(64) Patent No.: 6,617,333
Issued: Sep. 9, 2003
Appl. No.: 10/212,889
Filed: Aug. 6, 2002

U.S. Applications:
(62) Division of application No. 11/645,330, filed on Dec. 22, 2006, now abandoned, which is a division of application No. 11/222,485, filed on Sep. 8, 2005, now Pat. No. Re. 40,418.
(60) Provisional application No. 60/310,646, filed on Aug. 7, 2001.

(51) Int. Cl.
*A61K 31/47* (2006.01)
*A61K 31/00* (2006.01)
*A61K 31/44* (2006.01)

(52) U.S. Cl. ..... 514/291; 514/183; 514/311; 514/312; 514/313; 514/314

(58) Field of Classification Search ..... None
See application file for complete search history.

(56) References Cited

U.S. PATENT DOCUMENTS

| | | | |
|---|---|---|---|
| 3,929,992 | A | 12/1975 | Sehgal et al. |
| 3,993,749 | A | 11/1976 | Sehgal et al. |
| 4,193,983 | A | 3/1980 | Ullman et al. |
| 4,194,050 | A | 3/1980 | Hazama |

FOREIGN PATENT DOCUMENTS

| | | |
|---|---|---|
| EP | 0 448 078 | 9/1991 |
| EP | 0 525 960 B1 * | 3/1996 |
| EP | 0 722 720 | 7/1996 |
| EP | 0 525 960 | 2/2003 |
| SU | 415255 | 10/1974 |
| WO | WO 98/43960 | 10/1998 |
| WO | WO 02/13802 | 2/2002 |
| WO | WO 03/020266 | 3/2003 |
| WO | WO 2004/066919 A | 8/2004 |

OTHER PUBLICATIONS

Gura, Trish, Cancer Models: Systems for Identifying New Drugs are Often Faulty, Science, vol. 278, No. 5340, pp. 1041–1042 (Nov. 7, 1997).

(Continued)

*Primary Examiner*—Frederick Krass
*Assistant Examiner*—Benjamin Packard
(74) *Attorney, Agent, or Firm*—David A. Rubin, Esq; Howson & Howson LLP

(57) ABSTRACT

This invention provides the use of a combination of CCI-779 and EKB-569 in the treatment of neoplasms.

5 Claims, 5 Drawing Sheets

U.S. PATENT DOCUMENTS

| | | | |
|---|---|---|---|
| 4,195,021 | A | 3/1980 | Herron et al. |
| 4,401,653 | A | 8/1983 | Eng et al. |
| 4,478,959 | A | 10/1984 | Bechara |
| 4,565,843 | A | 1/1986 | Dunwald |
| 4,576,759 | A | 3/1986 | Viehe et al. |
| 4,664,825 | A | 5/1987 | Walsh |
| 4,885,171 | A | 12/1989 | Surendra et al. |
| 5,066,493 | A | 11/1991 | Sehgal et al. |
| 5,078,999 | A | 1/1992 | Warner et al. |
| 5,080,899 | A | 1/1992 | Sturm et al. |
| 5,100,899 | A | 3/1992 | Calne et al. |
| 5,206,018 | A | 4/1993 | Sehgal et al. |
| 5,286,730 | A | 2/1994 | Caufield et al. |
| 5,286,731 | A | 2/1994 | Caufield et al. |
| 5,288,711 | A | 2/1994 | Mitchell et al. |
| 5,321,009 | A | 6/1994 | Baeder et al. |
| 5,352,783 | A | 10/1994 | Shafiee et al. |
| 5,362,718 | A | 11/1994 | Skotnicki et al. |
| 5,387,589 | A | 2/1995 | Kulkami |
| 5,496,832 | A | 3/1996 | Armstrong et al. |
| 5,516,781 | A | 5/1996 | Morris et al. |
| 5,561,138 | A | 10/1996 | Armstrong et al. |
| 6,002,008 | A | 12/1999 | Wissner et al. |
| 6,277,983 | B1 | 8/2001 | Shaw et al. |
| 6,465,448 | B1 | 10/2002 | Gerson et al. |
| 6,617,333 | B2 | 9/2003 | Rabindran et al. |
| 6,664,288 | B1 | 12/2003 | Pardee et al. |
| 7,126,025 | B2 | 10/2006 | Considine et al. |
| 2004/0162442 | A1 | 8/2004 | Considine |

OTHER PUBLICATIONS

Alexandre, J. et al, Proc Am Assoc Cancer Res Annual Meeting (1999) vol. 41 March pp. 613.

Linneweh W., "γ–Butyrobetaine, crotonbetaine and carnitine in the animal metabolism", ACS abstract of Z. physiol. Chem., 1929, 181, c. 42–43.

Kiprianov A., "Reciprocal action between α–oxides and esters of amino acids", ACS abstract of Ukrainskii Khem. Zhurnal, 1926, 2, 2654–2655.

Sheludyakov V. et al., "Interaction of silyl and boroamines with ketene and diketene", ACS Abstract of Khimiya Geterostsiklicheskikh Soedinenii (1), 1967, c. 185–186.

Tsirk, A. et al, Stereoselectivities of the Intramolecular Diels–Alder Reaction in the Azanona and Azadecatriene series, Preparation of some Polyhydroisoindoles, Polyhydroisoquinolines, Decahydropyridol[2,1–α]isoindoles and Decahydro–2H–pyrido[1,2–b]isoquinolines. *Tetrahedron,* 54 (1998), 9529–9558.

Pages 1, 68 and 69 of Chinese Patent Application No. 1069492, published Mar. 3, 1993.

Gupta, RA, et al, "Combinations for Cancer Prevention", Nature Medicine, 6(9), pp. 974–978, Sep. 2000.

Torrance, C. et al, Combinatorial Chemoprevention of Intestinal Neoplasia, Nature Med., 6(9), pp. 1024–1028 (Sep. 2000).

Greenberger, LM, et al., Clin Cancer Res., vol. 6, p. 388 (Nov. 2000).

Georger, B. et al., "Antitumor Activity of the Rapamycin Analog CCI–779 in Human Primitive Neuroectodermal . . . ", Cancer Res., vol. 61, No. 4, pp. 1527–1532 (Feb. 15, 2001).

Vezina et al., Rapamycin (AY–22,989) A New Antifungal Antibiotic . . . , The Journal of Antibiotics, 28(10), 721–726 (Oct. 1975).

Sehgal, et al., "Rapamycin (AY–22,989) a New Antifungal Antibiotic, Fermentation . . . ", The Journal of Antibiotics, 28(10):727–732 (Oct. 1975).

Baker, et al, Rapamycin (AY–22,989), A New Antifungal Antibiotic, III. In vitro and In Vivo Evaluation, The Journal of Antibiotics, 31(6), 539–545 (Jun. 1978).

Calne, et al., Prolonged Survival of Pig Othotopic Heart Grafts Treated with Cyclosporin A, The Lancet, 1183–1185 (Jun. 1978).

Martel, et al., Inhibition of the Immune Response by Rapamycin, a New Antifungal Antibiotic, Can J Physiol Pharmacol, 55, 48–51 (Feb. 1977).

Staruch, et al, "FK506 and Rapamycin Inhibit Murine T Cell Activation Through Different Different Mechanism", The FASEB Journal, 3(3), (1989).

Dumont, et al, Rapamycin Blocks the Immunosuppressive Effect of FK506 But Not That of Cyclosporin A, The FASEB Journal, 3(4), 1989.

Marszak, I., et al, "Recherches Sur Les Aminoacides et Leurk Derives. I–Sur La Synthese Des Aminoacides a Partir Des Amine Tertiaries A Fonction Acetyleniqe Vria Amino Acids from Tertiary Amines Having a True Acetyl", Bulletin de la Societe Chimique de France, Societe Francaise de Chimie, 1959, pp. 182–185.

Marzsak et al, Amino Acids and their Derivatives. I. The Synthesis of Amino Acids from Tertiary Amines Having a True Acetylenic Function, CAOLD Abstract 282 h–I, (1960).

Johnson et al, "Relationships between drug activity in NCI preclinical in vitro and in vivo models and early clinical trials", British Journal of Cancer, 84(10): 1424–1431 (May 2001).

Balenovic, K., Contribution to the Knowledge of Gamma–Aminocrotonic Acid, J. Org. Chem. 19: 1589–1593 (1954).

Wissner, Allan, et al., Synthesis and Structure–Activity Relationship of 6,7–Disubstituted 4–Anilinoquinoline–3–Carbonitrile: The Design of an Orally Active, Irreversible Inhibitor of the Tyrosin Kinase Activity of the Epidermal Growth Factor Receptor and the Human Epidermal Growth Factor Receptor (HER–2), J Med. Chem., 46:49–63, Jan. 2, 2003.

* cited by examiner

ANTINEOPLASTIC COMBINATIONS

Matter enclosed in heavy brackets [ ] appears in the original patent but forms no part of this reissue specification; matter printed in italics indicates the additions made by reissue.

*CROSS-REFERENCE TO OTHER REISSUE APPLICATION*

*More than one reissue application has been filed for the reissue of U.S. Pat. No. 6,617,333. This application is a divisional of U.S. patent application Ser. No. 11/645,330, filed Dec. 22, 2006, which is a divisional of reissue application Ser. No. 11/222,485, filed Sep. 8, 2005.*

BACKGROUND OF THE INVENTION

This application claims priority from copending provisional application Serial No. 60/310,646, filed Aug. 7, 2001, the entire disclosure of which is hereby incorporated by reference.

This invention relates to the use of combinations of rapamycin 42-ester with 3-hydroxy-2-(hydroxymethyl)-2-methylpropionic acid (CCI-779) and 4-dimethylamino-but-2-enoic acid [4-(3-chloro-4-fluoro-phenylamino)-3-cyano-7-ethoxy-quinolin-6-yl]-amide (EKB-569).

Rapamycin is a macrocyclic triene antibiotic produced by Streptomyces hygroscopicus, which was found to have antifungal activity, particularly against Candida albicans, both in vitro and in vivo [C. Vezina et al., J. Antibiot. 28, 721 (1975); S. N. Sehgal et al., J. Antibiot. 28, 727 (1975) H. A. Baker et al., J. Antibiot. 31, 539 (1978); U.S. Pat. Nos. 3,929,992; and 3,993,749]. Additionally, rapamycin alone (U.S. Pat. No. 4,885,171) or in combination with picibanil (U.S. Pat. No. 4,401,653) has been shown to have antitumor activity.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899]. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

Rapamycin is also useful in preventing or treating systemic lupus erythematosus [U.S. Pat. No. 5,078,999], pulmonary inflammation [U.S. Pat. No. 5,080,899], insulin dependent diabetes mellitus [U.S. Pat. No. 5,321,009], skin disorders, such as psoriasis [U.S. Pat. No. 5,286,730], bowel disorders [U.S. Pat. No. 5,286,731], smooth muscle cell proliferation and intimal thickening following vascular injury [U.S. Pat. Nos. 5,288,711 and 5,516,781], adult T-cell leukemia/lymphoma [European Patent Application 525,960 A1], ocular inflammation [U.S. Pat. No. 5,387,589], malignant carcinomas [U.S. Pat. No. 5,206,018], cardiac inflammatory disease [U.S. Pat. No. 5,496,832], and anemia [U.S. Pat. No. 5,561,138].

Rapamycin 42-ester with 3-hydroxy-2-(hydroxymethyl)-2-methylpropionic acid (CCI-779) is ester of rapamycin which has demonstrated significant inhibitory effects on tumor growth in both in vitro and in vivo models. The preparation and use of hydroxyesters of rapamycin, including CCI-779, are disclosed in U.S. Pat. No. 5,362,718.

CCI-779 exhibits cytostatic, as opposed to cytotoxic properties, and may delay the time to progression of tumors or time to tumor recurrence. CCI-779 is considered to have a mechanism of action that is similar to that of sirolimus. CCI-779 binds to and forms a complex with the cytoplasmic protein FKBP, which inhibits an enzyme, mTOR (mammalian target of rapamycin, also known as FKBP12-rapamycin associated protein [FRAP]). Inhibition of mTOR's kinase activity inhibits a variety of signal transduction pathways, including cytokine-stimulated cell proliferation, translation of mRNAs for several key proteins that regulate the G1 phase of the cell cycle, and IL-2-induced transcription, leading to inhibition of progression of the cell cycle from G1 to S. The mechanism of action of CCI-779 that results in the G1→S phase block is novel for an anticancer drug.

In vitro, CCI-779 has been shown to inhibit the growth of a number of histologically diverse tumor cells. Central nervous system (CNS) cancer, leukemia (T-cell), breast cancer, prostate cancer, and melanoma lines were among the most sensitive to CCI-779. The compound arrested cells in the G1 phase of the cell cycle.

In vivo studies in nude mice have demonstrated that CCI-779 has activity against human tumor xenografts of diverse histological types. Gliomas were particularly sensitive to CCI-779 and the compound was active in an orthotopic glioma model in nude mice. Growth factor (platelet-derived)-induced stimulation of a human glioblastoma cell line in vitro was markedly suppressed by CCI-779. The growth of several human pancreatic tumors in nude mice as well as one of two breast cancer lines studied in vivo also was inhibited by CCI-779.

Protein tyrosine kinases are a class of enzymes that catalyze the transfer of a phosphate group of ATP or GTP to tyrosine residue located on protein substrates. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. However, under certain conditions, as a result of either mutation or overexpression, these receptors can become deregulated; the result of which is uncontrolled cell proliferation which can lead to tumor growth and ultimately to the disease known as cancer [Wilks A. F., Adv. Cancer Res., 60, 43 (1993) and Parsons, J. T.; Parsons, S. J., Important Advances in Oncology, DeVita V. T. Ed., J. B. Lippincott Co., Phila., 3 (1993)]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the erbB-2 (also referred to as the neu or HER2) oncogene. Since the phosphorylation event is a necessary signal for cell division to occur and since overexpressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, overexpression of the receptor kinase product of the erbB-2 oncogene has been associated with human breast and ovarian cancers [Slamon, D. J., et. al., Science, 244, 707 (1989) and Science, 235, 1146 (1987)]. Deregulation of EGF-R kinase has been associated with epidermoid tumors [Reiss, M., et. al., Cancer Res., 51, 6254 (1991)], breast tumors [Macias, A., et al., Anticancer Res., 7, 459 (1987)], and tumors involving other major organs [Gullick, W. J., Brit. Med. Bull., 47, 87 (1991)]. Because of the importance of the role played by deregulated receptor kinases in the pathogenesis of cancer, many recent studies have dealt with the development of specific PTK inhibitors as potential anti-cancer therapeutic agents [some recent reviews: Burke. T. R., Drugs Future, 17, 119 (1992) and Chang, C. J.; Geahlen, R. L., J. Nat. Prod., 55, 1529 (1992)].

4-Dimethylamino-but-2-enoic acid [4-(3-chloro-4-fluorophenylamino)-3-cyano-7-ethoxy-quinolin-6-yl]-amide (EKB-569) is an EGFR kinase inhibitor which has significant inhibitory effects on tumor growth in both in vitro and in vivo models. The preparation and use of EGFR kinase inhibitors, such as EKB-569, are disclosed in U.S. Pat. No. 6,002,008.

DESCRIPTION OF THE INVENTION

Figure 1:
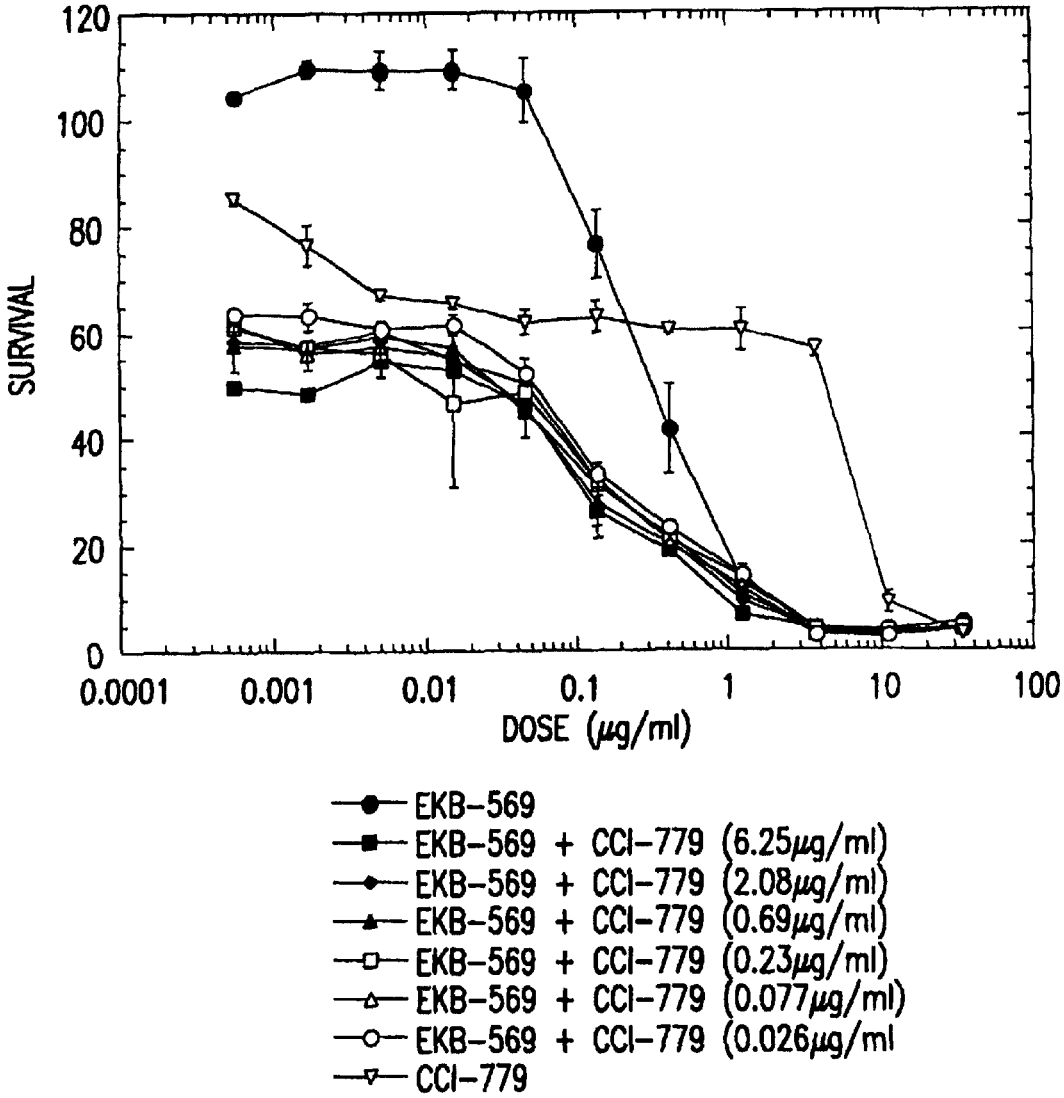
FIG. 1 shows cytotoxicity curves of EKB-569, CCI-779, and combinations of EKB-569+CCI-779 in HCT116 cells.

This invention provides the use of combinations of CCI-779 and EKB-569 as antineoplastic combination chemotherapy. In particular, these combinations are useful in the treatment of renal cancer, soft tissue cancer, breast cancer, neuroendocrine tumor of the lung, cervical cancer, uterine cancer, head and neck cancer, glioma, non-small lung cell cancer, prostate cancer, pancreatic cancer, lymphoma, melanoma, small cell lung cancer, ovarian cancer, colon cancer, esophageal cancer, gastric cancer, leukemia, colorectal cancer, and unknown primary cancer. This invention also provides combinations of CCI-779 and EKB-569 for use as antineoplastic combination chemotherapy, in which the dosage of either CCI-779 or EKB-569 or both are used in subtherapeutically effective dosages.

As used in accordance with this invention, the term "treatment" means treating a mammal having a neoplastic disease by providing said mammal an effective amount of a combination of CCI-779 and EKB-569 with the purpose of inhibiting growth of the neoplasm in such mammal, eradication of the neoplasm, or palliation of the mammal.

As used in accordance with this invention, the term "providing," with respect to providing the combination, means either directly administering the combination, or administering a prodrug, derivative, or analog of one or both of the components of the combination which will form an effective amount of the combination within the body.

The preparation of CCI-779 is described in U.S. Pat. No. 5,362,718, which is hereby incorporated by reference. An improved preparation of CCI-779 is disclosed in U.S. patent application Ser. No. 09/670,358, now U.S. Pat. No. 6,277,983, which is hereby incorporated by reference. When CCI-779 is used as an antineoplastic agent, it is projected that initial i.v. infusion dosages will be between about 0.1 and 100 mg/m$^2$ when administered on a daily dosage regimen (daily for 5 days, every 2–3 weeks), and between about 0.1 and 1000 mg/m$^2$ when administered on a once weekly dosage regimen. Oral or intravenous infusion are the preferred routes of administration, with intravenous being more preferred.

EKB-569 can be prepared according to the procedures described in U.S. Pat. No. 6,002,008, which is incorporated by reference. Preferred procedures for the preparation of EKB-569 are provided herein. When EKB-569 is used as an antineoplastic agent it is projected that the initial oral dosage will be between 1 and 100 mg per day. Depending on patient tolerance, EKB-569 can be administered daily for a treatment period, such as 14 days, followed by a rest period (no drug administered), or can be administered on a continuous basis for a longer treatment period (for example, 6 months or longer).

The antineoplastic activity of the CCI-779 plus EKB-569 combination was confirmed in in vitro standard pharmacological test procedure; the following briefly describes the procedure used and the results obtained.

Cell Proliferation Procedure—HCT 116 colon adenocarcinoma cells were maintained in RPMI 1640 medium (Life Technologies, Inc., Gaithersburg, Md.) supplemented with 10% fetal bovine serum (FBS, Life Technologies) and 50 μg/ml gentamicin (Life Technologies) under 7% $CO_2$ at 37° C. Cells were plated in 96-well microtiter dishes (6000 cells/well) in 200 μl RPMI 1640 medium containing 5% FBS and 50 μg/ml gentamicin and incubated overnight at 37° C. Compound dilutions were prepared in the same medium, at 5× final concentration, and 50 μl of the drug dilution was added to the cell-containing wells. For studies involving combinations of two drugs, serial dilutions of one compound were prepared in the presence of a fixed dose of a second compound. Alternatively, a checkerboard dilution series was employed. Cells were cultured for three days in the presence of the drugs. Untreated cells were included as controls. The percentage of surviving cells was determined using sulforhodamine B (SRB, Sigma-Aldrich, St Louis, Mo.), a protein binding dye. Cellular protein was precipitated in each well by the addition of 50 μl of 50% cold trichloroacetic acid. After 1 hour, the plates were washed extensively in water and dried. SRB dye reagent (0.4% SRB in 1% acetic acid, 80 μl per well) was added and plates were kept at room temperature for ten minutes. Plates were then washed thoroughly in 1% acetic acid and dried. Cell-associated dye was dissolved in 10 mM Tris (150 μl) and the absorbance was read at 540 nm in a microtiter plate reader. The concentration of compound that caused a fixed percentage inhibition of growth was determined by plotting cell survival (relative to untreated cells) against the compound dose.

Synergy Evaluation—Isobolograms were used to study the interaction of two pharmacological agents. Here, the concentration of each drug alone which produces a certain endpoint (e.g 50% inhibition of cell growth, $IC_{50}$), is plotted on the two graphical axes. The straight line connecting the two points represents equally effective concentrations of all combinations of the two drugs if the interaction is purely additive. A shift of the isobologram to the left of the predicted cytotoxicity (curve with concave side up) represents a synergistic interaction. Conversely, a shift to the right (isobologram with the convex side up) represents an antagonistic interaction. When isobolograms for different endpoints were plotted on the same graph, the concentration of each drug was expressed as the fraction of the concentration of each drug alone that produced the same effect. This produces a symmetrical isobologram with unit-less measures on each axis, and allows a direct comparison of different endpoints.

A second model for studying drug interactions was proposed by Prichard and Shipman [Antiviral Research. 14:181–206 (1990)]. This is a 3-dimensional model: one for each drug and the third for the biological effect. Theoretical additive interactions are calculated from the individual dose-response curves, based on a dissimilar sites model of additivity (Bliss independence). The calculated additive surface, representing predicted cytotoxicity is subtracted from the experimental surface to reveal areas of enhanced toxicity (synergy) or reduced toxicity (antagonism). The resulting surface appears as a horizontal plane at 0% inhibition above the calculated additive surface, if the interaction is additive. Peaks and valleys deviating from this plane are indicative of synergy and antagonism, respectively. MacSynergyII, a Microsoft Excel-based software was used to perform all calculations automatically. This spreadsheet calculates the theoretical additive interactions, and locates and quantifies synergistic or antagonistic interactions that are significant at the 95% confidence levels. The results were plotted as a 3-dimensional plot, or as a contour plot.

Figure 2:
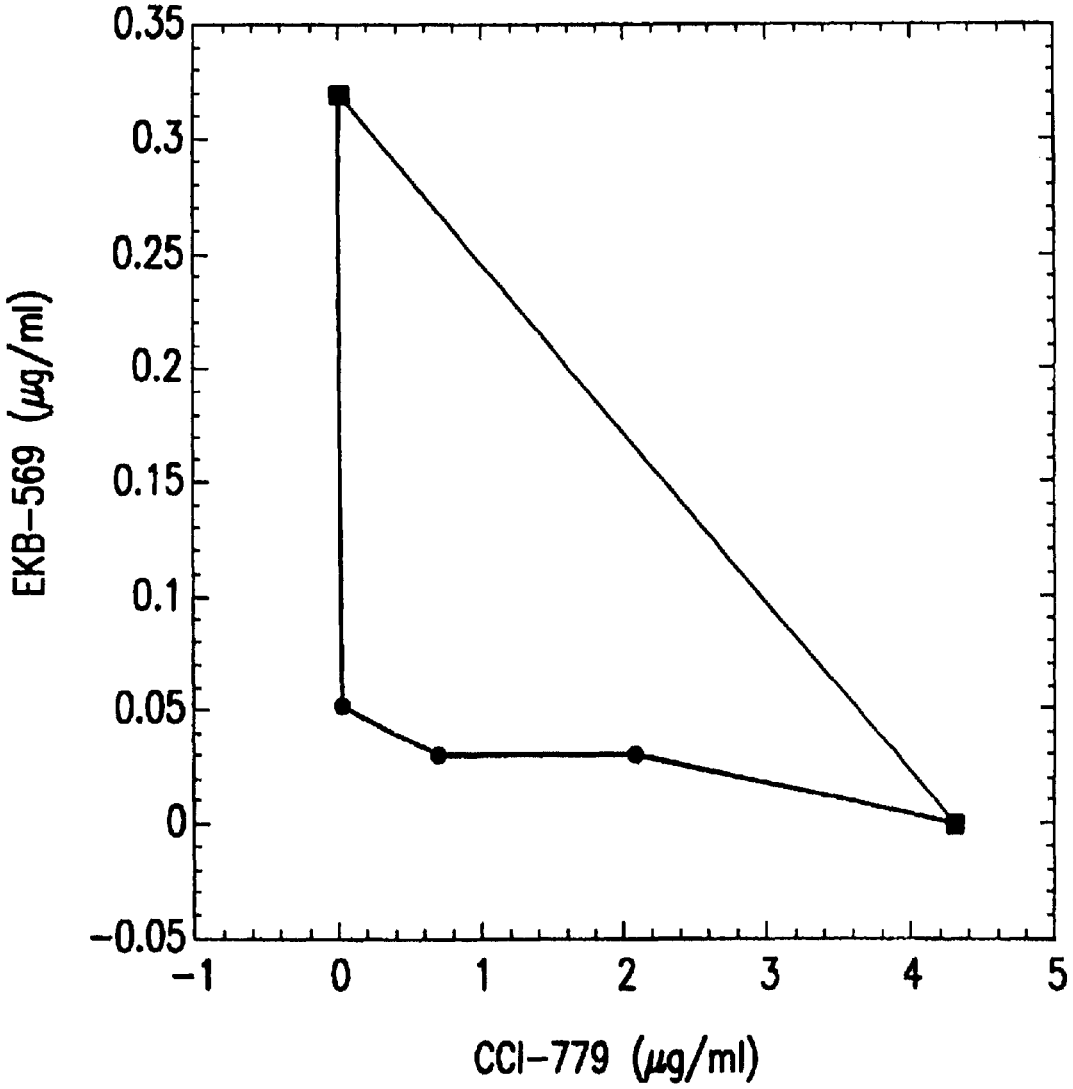
FIG. 2 shows isobolograms (at the 50% effect level) of a EKB-569+CCI-779 combination.
Figure 3:
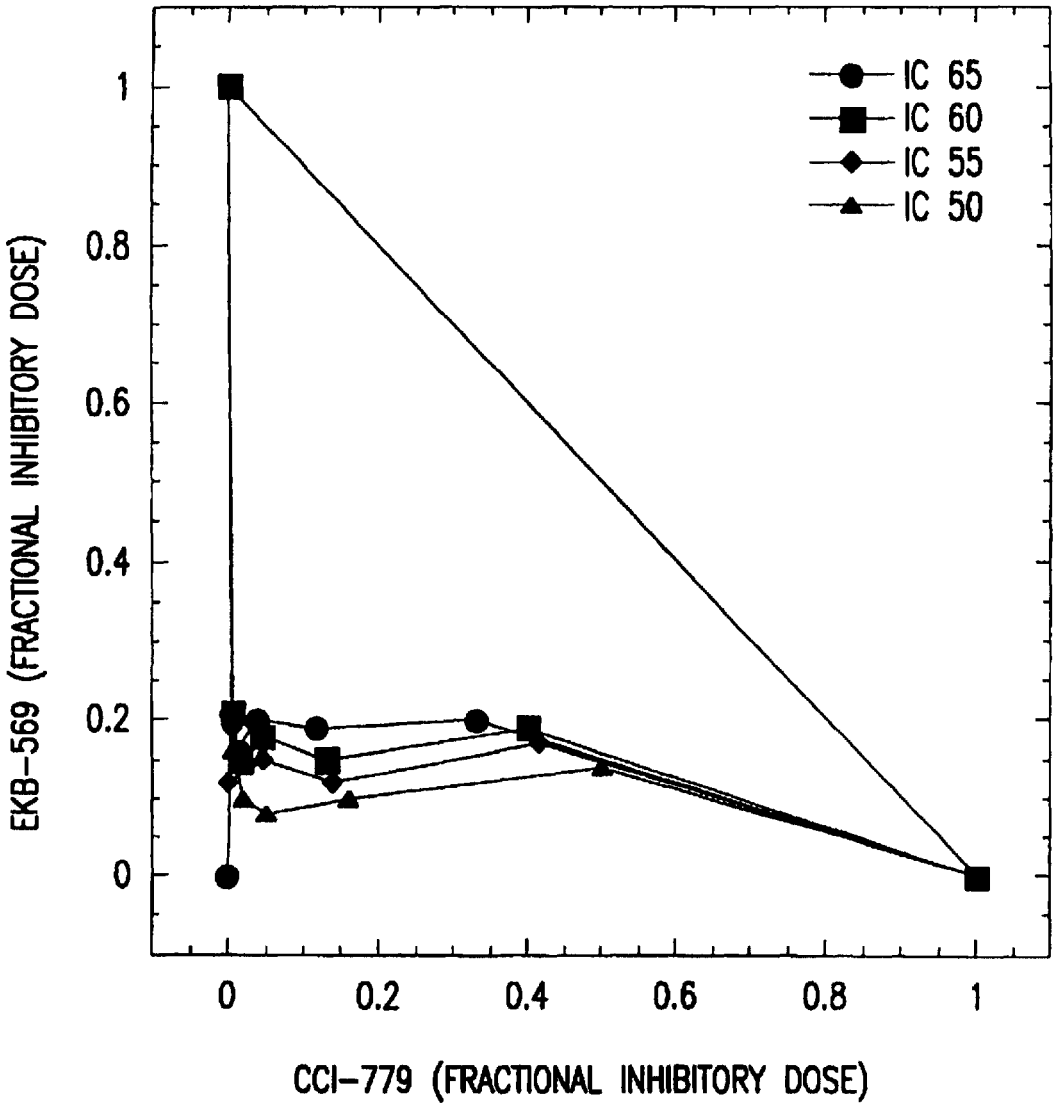
FIG. 3 shows isobolograms for EKB-569+CCI-779 combinations derived from different endpoints ranging from 50–65%.

Results—HCT 116 cells were chosen as they express low, but detectable levels of EGFR, and are sensitive to inhibition by EGFR inhibitors. The cells are somewhat resistant to CCI-779, but are inhibited by high doses (5–10 μg/ml) of this drug. HCT-116 cells were cultured in the presence of EKB-569 alone, CCI-779 alone, or a dilution series of EKB-569 with fixed doses of CCI-779. Following growth for 3 days, cell survival was determined using the SRB test procedure. Cytotoxicity curves are shown in FIG. 1. EKB-569 produced an $IC_{50}$ value of 0.31 μg/ml in HCT116 cells. When this compound was combined with 2.08 μg/ml CCI-779 (which caused 41% inhibition of growth when administered alone), the $IC_{50}$ value is reduced to 0.03 μg/ml, a 10-fold decrease. When combined with 0.026 μg/ml CCI-779 (which alone inhibits cell proliferation by 36%), the $IC_{50}$ value dropped to 0.051 μg/ml, a 6-fold decrease. Similar results were observed when dose-response curves were produced with CCI-779 in the presence of fixed doses of EKB-569. To identify the nature of this drug interaction, isobolograms (at 50% effect level) of the combination of EKB-569 and CCI-779 were generated (FIG. 2). The isobologram was deeply indented with the concave side up, indicating a substantial synergistic interaction between the two drugs. At the most synergistic point, 0.03 μg/ml of EKB-569 combined with 0.077 μg/ml CCI-779 was iso-effective with 0.31 μg/ml of EKB-569 alone or 4.3 μg/ml CCI-779 alone ($IC_{50}$ for each drug alone). Thus, a 10-fold reduction in the dose of EKB-569 and a 50-fold reduction in the dose of CCI-779 was required to inhibit cell proliferation by 50% when the drugs were combined, compared to either drug alone. Isobolograms derived from different endpoints, ranging from 50 to 65% were also examined. As shown in FIG. 3., the isobolograms produced were almost superimposable, indicating synergy at all effect levels tested.

Figure 4:
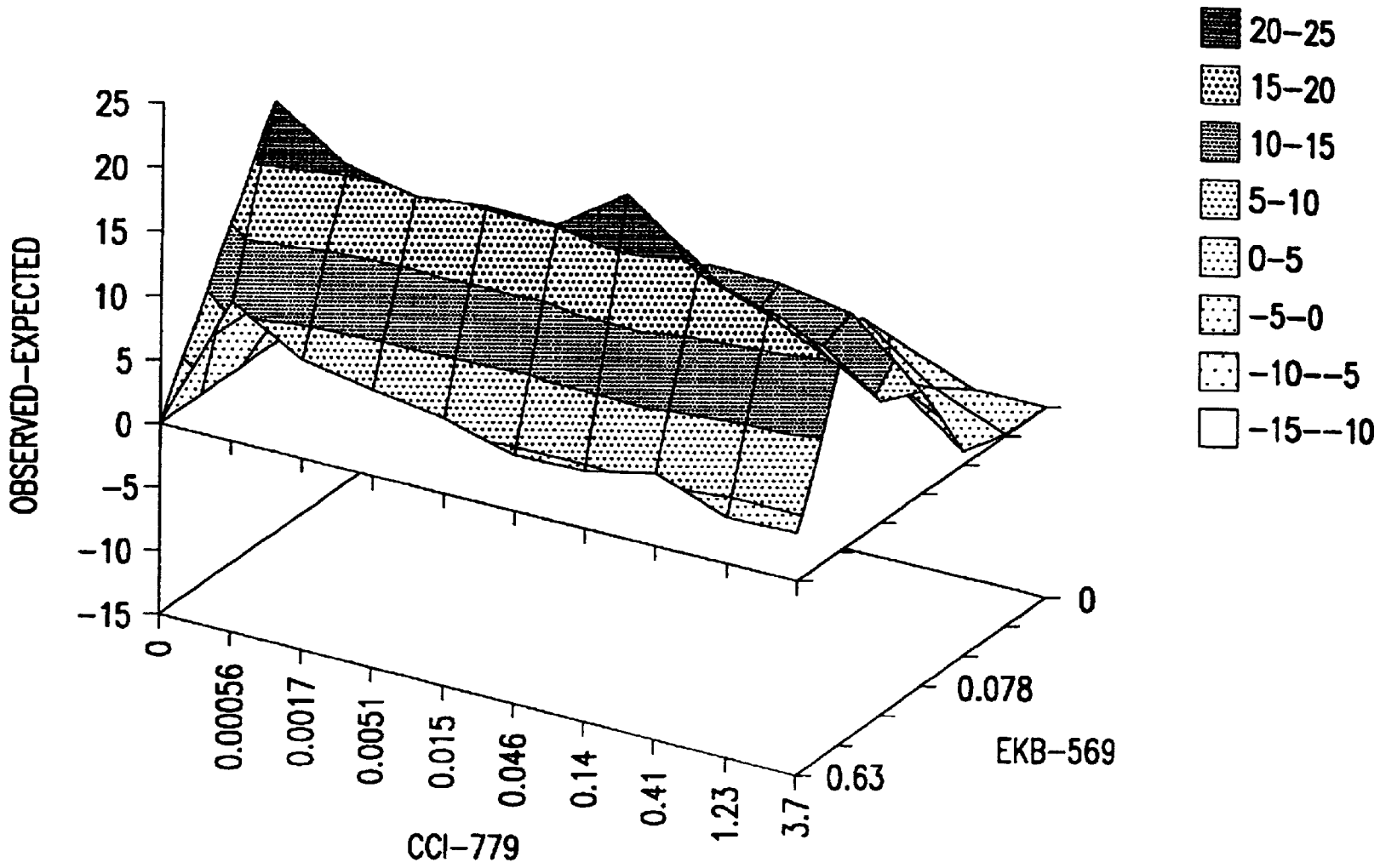
FIG. 4 shows a 3-dimensional analysis of the synergistic interaction of a EKB-569+CCI-779 combination.
Figure 5:
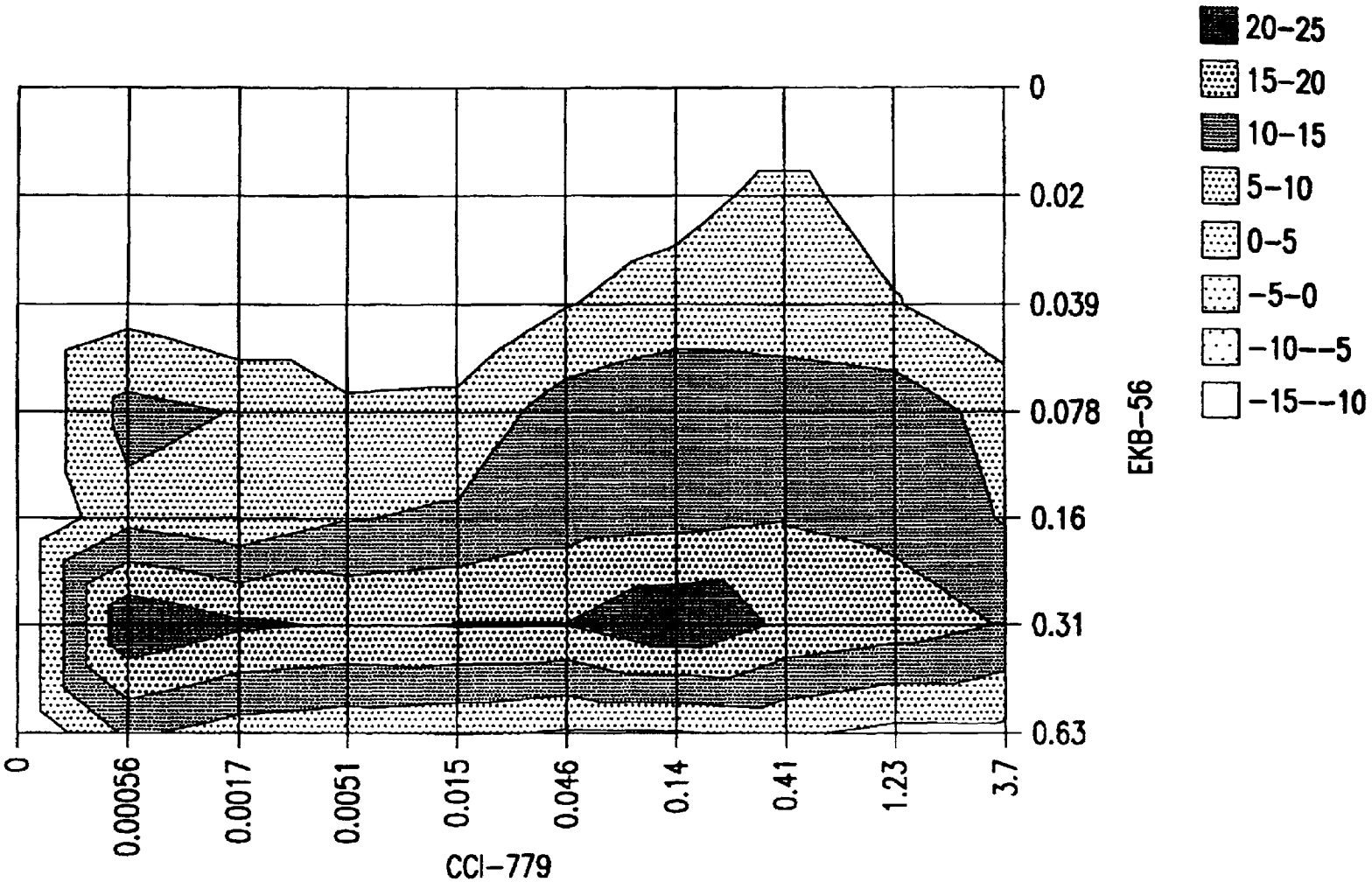
FIG. 5 shows a contour plot of the 3-dimensional synergy plot of a EKB-569+CCI-779 combination.

The interaction between EKB-569 and CCI-779 was also evaluated using a 3-dimensional analysis. Here, pharmacological interactions are presented in a 3-dimensional plot with the plane at 0% representing additive interaction, and peaks and valleys representing areas of synergy or antagonism, respectively, between the two drugs. In FIG. 4, the combination of EKB-569 and CCI-779 resulted in a broad area of synergistic interaction, consistent with the results shown in the isobologram studies. A contour plot of the 3-dimensional synergy plot facilitates the identification of the concentrations of drugs at which greatest synergistic toxicity occurs (FIG. 5). A broad area of synergy was observed at 0.0005 to 3 μg/ml CCI-779 and 0.16 to 0.4 μg/ml EKB-569. Within this area, two peaks of maximum synergy occurred at 0.0005 to 0.003 μg/ml and 0.05 to 0.3 μg/ml of CCI-779 and 0.25 to 0.37 μg/ml EKB-569.

Based on the results of these standard pharmacological test procedures, combinations of CCI-779 plus EKB-569 acted synergistically together, and are useful as antineoplastic therapy. More particularly, these combinations are useful in the treatment of renal carcinoma, soft tissue sarcoma, breast cancer, neuroendocrine tumor of the lung, cervical cancer, uterine cancer, head and neck cancer, glioma, non-small cell lung cancer, prostate cancer, pancreatic cancer, lymphoma, melanoma, small cell lung cancer, ovarian cancer, colon cancer, esophageal cancer, gastric cancer, leukemia, colorectal cancer, and unknown primary cancer. As these combinations contain at least two active antineoplastic agents, the use of such combinations also provides for the use of combinations of each of the agents in which one or both of the agents is used at subtherapeutically effective dosages, thereby lessening toxicity associated with the individual chemotherapeutic agent.

In providing chemotherapy, multiple agents having different modalities of action are typically used as part of a chemotherapy "cocktail." It is anticipated that the combinations of this invention will be used as part of a chemotherapy cocktail that may contain one or more additional antineoplastic agents depending on the nature of the neoplasia to be treated. For example, this invention also covers the use of the CCI-779/EKB-923 combination used in conjunction with other chemotherapeutic agents, such as antimetabolites (i.e., 5-fluorouracil, floxuradine, thioguanine, cytarabine, fludarabine, 6-mercaptopurine, methotrexate, gemcitabine, capacitabine, pentostatin, trimetrexate, or cladribine); DNA crosslinking and alkylating agents (i.e., cisplatin, carboplatin, streptazoin, melphalan, chlorambucil, carmustine, methclorethamine, lomustine, bisulfan, thiotepa, ifofamide, or cyclophosphamide); hormonal agents (i.e., tamoxifen, roloxifen, toremifene, anastrozole, or letrozole); antibiotics (i.e., plicamycin, bleomycin, mitoxantrone, idarubicin, dactinomycin, mitomycin, doxorubicin or daunorubicin); immunomodulators (i.e., interferons, IL-2, or BCG); antimitotic agents (i.e., estramustine, paclitaxel, docetaxel, vinblastine, vincristine, or vinorelbine); topoisomerase inhibitors (i.e., topotecan, irinotecan, etoposide, or teniposide.); and other agents (i.e., hydroxyurea, trastuzumab, altretamine, retuximab, L-asparaginase, or gemtuzumab ozogamicin).

As used in this invention, the combination regimen can be given simultaneously or can be given in a staggered regimen, with CCI-779 being given at a different time during the course of chemotherapy than EKB-923. This time differential may range from several minutes, hours, days, weeks, or longer between administration of the two agents. Therefore, the term combination does not necessarily mean administered at the same time or as a unitary dose, but that each of the components are administered during a desired treatment period. The agents may also be administered by different routes. For example, in the combination of CCI-779 plus EKB-569, it is anticipated that the CCI-779 will be administered orally or parenterally, with parenterally being preferred, while the EKB-569 may be administered parenterally, orally, or by other acceptable means. These combination can be administered daily, weekly, or even once monthly. As typical for chemotherapeutic regimens, a course of chemotherapy may be repeated several weeks later, and may follow the same timeframe for administration of the two agents, or may be modified based on patient response.

As typical with chemotherapy, dosage regimens are closely monitored by the treating physician, based on numerous factors including the severity of the disease, response to the disease, any treatment related toxicities, age, health of the patient, and other concomitant disorders or treatments.

Based on the results obtained with the CCI-779 plus EKB-569 combinations, it is projected that the initial i.v. infusion dosage of CCI-779 will be between about 0.1 and 100 mg/m$^2$, with between about 2.5 and 70 mg/m$^2$ being preferred. It is also preferred that the CCI-779 be administered by i.v., typically over a 30 minute period, and administered about once per week. The initial daily dosages of EKB-569 will be between about 1 and 100 mg, with between 5 and 75 mg being preferred. After one or more treatment cycles, the dosages can be adjusted upwards or downwards depending on the results obtained and the side effects observed.

Oral formulations containing the active compounds of this invention may comprise any conventionally used oral forms, including tablets, capsulates, buccal forms, troches, lozenges and oral liquids, supsensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The following provides the preparation of EKB-569 from commercially available starting materials or starting materials that can be made according to available literature procedures.

Preparation of 4-dimethylaminocrotonic acid from TMS-4-bromocrotonate

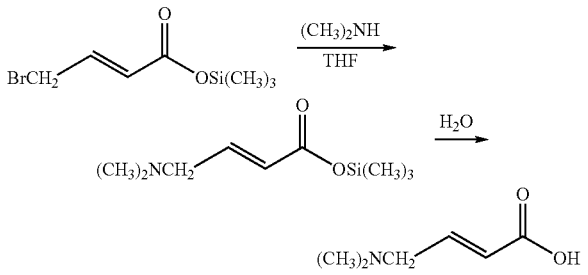

211 ml dimethylamine (2M in THF, 0.422 moles) was added drop-wise to a solution of 50 g TMS-4-bromocrotonate (0.211 moles, 75.9% by GC-MS) in 250 ml of THF at 0–50 C. under $N_2$. The reaction mixture was stirred at room temperature for 30 minutes. A white solid by-product was filtered off. 2 ml water was added to the filtrate followed by seeding. The crystals formed were filtered and washed with ether to give 18.3 g (from two crops) off-white solid product. Yield was 67.2% (98% purity by GC-MS, NMR was consistent with the structure).

Preparation of methyl 4-dimethylaminocrotonate from methyl-4-bromocrotonate

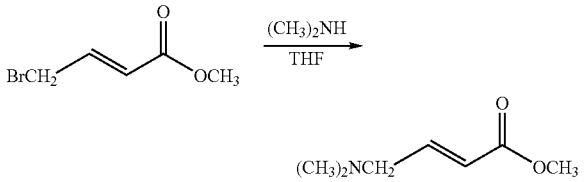

120 ml dimethylamine (2M in THF, 0.24 moles) was added drop-wise to a solution of 20 g methyl 4-bromocrotonate (85% purity), 0.095 moles) in 150 ml of THF at 0–50 C. under $N_2$. The reaction mixture was stirred for 15 minutes at room temperature. TLC (9:1 $CH_2Cl_2$:MeOH with few drops of $Et_3N$) showed residual methyl 4-bromocrotonate. The reaction mixture was heated to 40–450 C. for 15 minutes. A white solid by-product was filtered off. The filtrate was evaporated to give a yellow oil (14 g). The yellow oil was dissolved in 100 ml $CH_2Cl_2$ and washed with $H_2O$ twice. The aqueous layer was back extracted with 100 ml $CH_2Cl_2$. The $CH_2Cl_2$ layers were combined, dried over $MgSO_4$ and filtered. The filtrate was evaporated to give an oil (12 g). Yield was 88%. NMR indicated desired product with trace methyl 4-bromocrotonate.

Preparation of Methyl 4-N,N-dimethylaminocrotonate hydrochloride on large scale

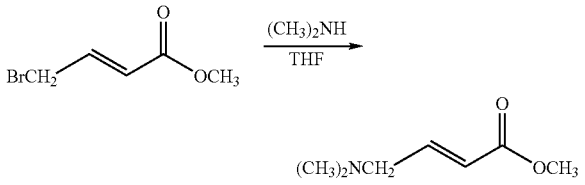

A 3 L flask was charged with tetrahydrofuran (0.71 kg, 0.80 L). Methyl 4-bromocrotonate (0.20 kg, 0.13 L, d=1.522 g/mL) was added and rinsed with tetrahydrofuran (0.18 kg, 0.20 L). The solution was stirred and cooled to 0–10° C. An additional funnel was charged with a solution of dimethylamine in tetrahydrofuran and added over (1 h 15 min) keeping the temperature at 0–10° C. The mixture was stirred for a minimum of 30 mins and checked for reaction completion by TLC. The reaction was complete when there is ≦2% detectable starting material (methyl 4-bromocrotonate) present. The mixture was filtered cold on a Buchner funnel into a 3 L multi-neck flask, rinsed with pre-chilled (0–10° C.) tetrahydrofuran (2×0.18 kg, 2×0.20 L), and suction maintained until dripping stops. The flask was equipped with an agitator, thermometer, and a setup for vacuum distillation. The solution was concentrated by distillation under a reduced pressure of (125–200 mm Hg) and at a maximum pot temperature of (40° C.) to a pot volume of (200 mL). Isopropanol (0.22 kg, 0.28 L) was added and the mixture cooled to 0–10° C. The distillation stillhead was replaced with an addition funnel charged with a solution of HCl in isopropanol, which was added over 45 min until pH of 2.0–3.0 was reached, while maintaining a temperature 0–10° C. The mixture was held for a minimum 30 min, and fileted cold on a Buchner funnel, rinsed with isopropanol (2×0.12 kg, 2×0.15 L). The filter cake was dammed and suction maintained until dripping stopped. The product was dried in a vacuum oven at 50° C. and 10 mm Hg for 18–20 h.

Preparation of 4-dimethylaminocrotonic acid hydrochloride from methyl 4-dimethylaminocrotonate

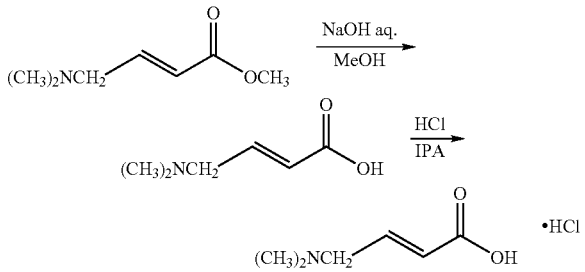

A NaOH solution (3.35 g in 25 ml $H_2O$, 0.084 moles) was added drop-wise to a solution of 12 g methyl 4-dimethylaminocrotonate (0.084 moles) in 100 ml MeOH at room temperature. The reaction mixture was heated to 40–45° C. for 1 hour then cooled to room temperature. The pH was adjusted to 1–2 with 5 N HCl. The mixture was concentrated to a thick oil which was triturated with dehydrated alcohol to form a solid. The solid by-product was filtered off. The filtrate was evaporated to an oil which was triturated with IPA. Seven (7.0) g of white solid product was obtained. Yield was 50% with the purity 86.3% by GC-MS.

Preparation of 4-N,N-dimethylaminocrotonic acid hydrochloride on large scale

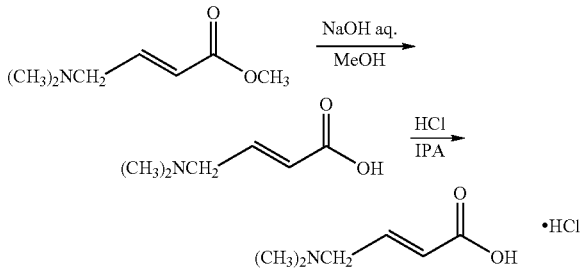

A 2 L multi-neck flask was equipped with agitator, thermometer, addition funnel, and nitrogen protection. The flask was charged with ethanol (0.39 kg, 0.50 L). Methyl 4-N,N-dimethylamino crotonate hydrochloride (0.125 kg) was added and rinsed with ethanol (0.10 kg, 0.125 L). The suspension was stirred and cooled to 0–10° C. The addition funnel was charged with sodium hydroxide (50%) (0.11 kg, 0.072 L, d=1.53 g/mL) and addd over 20 min keeping the temperature at 0–10° C. A slight exotherm was observed and the mixture turned yellow. The mixture was stirred for a minimum of 15 min, and then warmed to 18–22° C., and held for a minimum of 4 h. The reaction was checked for completion by TLC. The reaction is complete when there is ≦2% detectable starting material (methyl 4-N,N-dimethylaminocrotonate hydrochloride) present. The mixture was cooled to 0–10° C. An addition funnel was charged with a solution of HCl in isopropanol and added over 40 min until pH 2.0–3.0 was attained, while maintaining the pot temperature of 0–10° C. The mixture was sturred for a minimum of 30 min, and filtered cold on a Buchner funnel into a 2 L multi-neck flask, rinsed with cold ethanol (0–10° C.) (2×0.05 kg, 2×0.063 L) with suction maintained until dripping stops. The flask was equpped with an agitator, thermometer, and setup for vacuum distillation. Solvent was removed under a reduced pressure of 50–100 mm Hg and at a maximum pot temperature of (40° C.) to a pot volume of 160–180 mL. Isopropanol (0.049 kg, 0.063 L) was added, and the mixture warmed to 35–40° C. over 10 min. Acetone (0.10 kg, 0.13 L) was added over 20 min while maintaining the pot temperature at 35–40° C. The mixture was seeded and cooled to ambient temperature 20–25° C., and held there for a minimum of 12–18 h. The mixture was cooled to 0–10° C., held there for a minimum of 1 h. A mixture of isopropanol (0.049 kg, 0.063 L) and acetone (0.10 kg, 0.13 L) was prepared, stirred to homogenize, and cooled to 0–10° C. The mixture was filtered cold on a Buchner funnel, rinsed with isopropanol/acetone (2×0.074 kg, 2×0.096 L), and the filter caked dammed while maintaining suction until dripping stopped. The product was dried in a vacuum oven at 50° C. and 10 mm Hg for 18–20 h.

Preparation of 4-dimethylaminocrotonyl anilide from 4-dimethylaminocrotonic acid hydrochloride

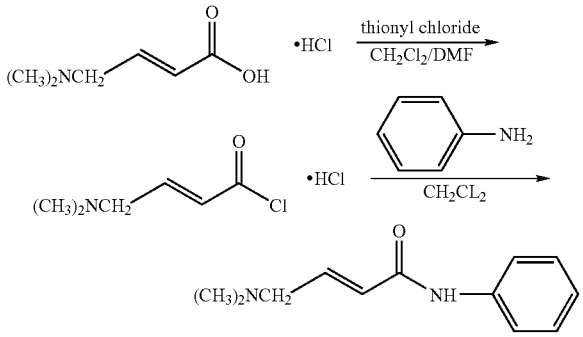

Thionyl chloride (0.36 ml, 0.005 moles) was added drop-wise to a solution of 0.33 g 4-dimethylaminocrotonic acid hydrochloride (0.002 moles) in 15 ml $CH_2Cl_2$ containing 2 drops of DMF at 0° C. under N2. The reaction mixture was refluxed for 30 min. The 0.72 ml aniline (0.008 moles) was added drop-wise to the reaction mixture at 0° C. and stirred for 1 hour at room temperature. A solid by-product was filtered. The filtrate was evaporated to give an oil (0.6 g). GC-MS data shows that the oil is 11.7% 4-dimethylaminocrotonic acid hydrochloride and 85% of desired product.

Preparation and isolation of 4-N,N-dimethylaminocrotonoylchloride hydrochloride

A well stirred suspension 4-dimethylaminocrotonic acid hydrochloride (5.0 g, 30 mmol) in cold (0° C.) THF (40 mL) and DMF (2 pipet drops) was treated with oxalyl chloride (3.15 mL, 36 mmol). The mixture was stirred at 20–25° C. for 3 h then cooled to 0° C. and held for 30 min. The solids were collected on Buchner funnel (under a blanket of nitrogen) and washed with cold (0° C.) THF (3×5 mL). The product was dried under vacuum (~1 torr) at 40–50 2° C. for 3 h to give 4.0 g of 4-dimethylaminocrotonoyl chloride hydrochloride. This material is characterized as its methyl ester by treatment of the solid with methanol.

Alternatively, the title compound can be prepared in $CH_3CN$ and used directly for the coupling step:

Preparation of EKB-569

A 3 L multi-neck flask was equipped with an agitator, thermometer, dip tube, and nitrogen protection. The flask was charged with N-methyl pyrrolidinone (0.77 kg, 0.75 L, d=1.033 g/mL). At ambient temperature, 4-[3-chloro-4-fluorophenyl]amino-6-amino-3-cyano-7-ethoxy quinoline (0.0748 kg) [see, U.S. Pat. No. 6,002,008] was added and the mixture stirred while heating to 40–45° C. and held for 15 min. The flask was cooled to 0–10° C. The mixture containing 4-N,N-dimethylaminocrotonoyl chloride hydrochloride was transferred via dip tube and positive nitrogen pressure to the 3 L flask over 30–45 min, while maintaining 0–10° C. The mixture was kept at 0–10° C. for a minimum of 2 h. The reaction was checked for completion by HPLC. The reaction is completion when there is ≦2% of the starting material (4-[3-chloro-4-fluorophenyl]amino-6-amino-3-cyano-7-ethoxy quinoline) present. A 12 L multi-neck flask equipped with agitator, thermometer, dip tube, and nitrogen protection was charged with water (2.61 kg, 2.61 L). Sodium bicarbonate (0.209 kg) was added and stirred until a solution was obtained. The solution was cooled to 20–24° C. The NMP-$CH_3CN$ mixture was transferred, via dip tube and positive nitrogen pressure, to the 12 L flask over 45–60 min, while maintaining 20–24° C. The mixture was maintained at 20–24° C. for a minimum of 1 h, and filtered on a Buchner funnel, and rinsed with water (3×0.40 kg, 3×0.40 L) with suction being maintained until dripping stops. The product was dried in a vacuum oven at 50° C. and 10 mm Hg for 28–30 h to give 78.5 g (86% yield) of product.

What is claimed is:

[1. A method of treating a neoplasm in a mammal in need thereof, which comprises providing to said mammal synergistically effective amount of a combination comprising CCI-779 and EKB-569.]

[2. The method according to claim 1, wherein the neoplasm is renal cancer.]

[3. The method according to claim 1, wherein the neoplasm is soft tissue sarcoma.]

[4. The method according to claim 1, wherein the neoplasm is breast cancer.]

[5. The method according to claim 1, wherein the neoplasm is a neuroendocrine tumor of the lung.]

[6. The method according to claim 1, wherein the neoplasm is cervical cancer.]

[7. The method according to claim 1, wherein the neoplasm is uterine cancer.]

[8. The method according to claim 1, wherein the neoplasm is a head and neck cancer.]

[9. The method according to claim 1, wherein the neoplasm is glioma.]

[10. The method according to claim 1, wherein the neoplasm is non-small cell lung cancer.]

[11. The method according to claim 1, wherein the neoplasm is prostate cancer.]

[12. The method according to claim 1, wherein the neoplasm is pancreatic cancer.]

[13. The method according to claim 1, wherein the neoplasm is lymphoma.]

[14. The method according to claim 1, wherein the neoplasm is melanoma.]

[15. The method according to claim 1, wherein the neoplasm is small cell lung cancer.]

[16. The method according to claim 1, wherein the neoplasm is ovarian cancer.]

[17. The method according to claim 1, wherein the neoplasm is colon cancer.]

[18. The method according to claim 1, wherein the neoplasm is esophageal cancer.]

[19. The method according to claim 1, wherein the neoplasm is gastric cancer.]

[20. The method according to claim 1, wherein the neoplasm is leukemia.]

[21. The method according to claim 1, wherein the neoplasm is colorectal cancer.]

[22. The method according to claim 1, wherein the neoplasm is unknown primary cancer.]

[23. A method of treating a neoplasm in a mammal in need thereof, which comprises providing to said mammal an effective amount of a synergistic combination comprising CCI-779 and EKB-569, wherein either CCI-779, EKB-569, or both are provided in subtherapeutically effective amounts.]

[24. The method according to claim 23 in which CCI-779 is provided in a subtherapeutically effective amount.]

[25. The method according to claim 23 in which EKB-569 is provided in a subtherapeutically effective amount.]

[26. The method according to claim 23 in which both CCI-779 and EKB-569 are provided in subtherapeutically effective amounts.]

[27. An antineoplastic combination which comprises an antineoplastic effective amount of a synergistic combination of CCI-779 and EKB-569.]

*28. A process for the preparation of a compound of formula:*

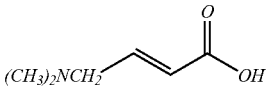

*or a HCl salt thereof,*

*comprising:*

(*a*) *reacting a trimethylsilyl-4-bromocrotonate or methyl 4-bromocrotonate with dimethylamine to obtain the corresponding 4-dimethylaminocrotonate;*

(*b*) *hydrolyzing the 4-dimethylaminocrotonate of step* (*a*) *to form the corresponding 4-dimethylaminocrotonic acid; and*

(*c*) *optionally chlorinating the compound of step* (*b*) *to form the HCl salt of the compound of step* (*b*).

*29. The process according to claim 28, wherein the hydrolyzing step* (*c*) *comprises reacting the 4-dimethylaminocrotonate with NaOH in the presence of MeOH.*

*30. The process according to claim 28, wherein the chlorinating step* (*c*) *comprises reacting the 4-dimethylaminocrotonic acid with HCl.*

*31. The process according to claim 28 wherein the reaction is performed with trimethylsilyl-4-bromocrotonate.*

*32. The process according to claim 28 wherein the reaction is performed with methyl 4-bromocrotonate.*

* * * * *